United States Patent [19]
Brown

[11] Patent Number: 6,113,578
[45] Date of Patent: Sep. 5, 2000

[54] OPTICAL DOSE MEASUREMENTS IN SYRINGES

[75] Inventor: Stephen J. Brown, Woodside, Calif.

[73] Assignee: Health Hero Network, Inc., Mountain View, Calif.

[21] Appl. No.: 09/359,166

[22] Filed: Jul. 21, 1999

Related U.S. Application Data

[60] Division of application No. 08/898,711, Jul. 22, 1997, abandoned, which is a continuation-in-part of application No. 08/681,223, Jul. 22, 1996, Pat. No. 5,792,117, and a continuation-in-part of application No. 08/278,929, Jul. 22, 1994, Pat. No. 5,569,212.

[51] Int. Cl.[7] ................................................. A61M 5/00
[52] U.S. Cl. ........................ 604/207; 604/246; 222/23; 222/30
[58] Field of Search .................................. 604/207, 246; 235/465; 22/23, 30

[56] References Cited

U.S. PATENT DOCUMENTS

| | | | |
|---|---|---|---|
| 4,853,521 | 8/1989 | Claeys et al. | 235/375 |
| 4,950,246 | 8/1990 | Muller | 604/154 |
| 4,978,335 | 12/1990 | Arthur, III . | |
| 5,009,645 | 4/1991 | Silver et al. | 604/207 |
| 5,019,974 | 5/1991 | Beckers | 364/413.02 |
| 5,104,380 | 4/1992 | Holman et al. | 604/117 |
| 5,176,502 | 1/1993 | Sanderson et al. | 417/18 |
| 5,226,895 | 7/1993 | Harris | 604/208 |
| 5,307,263 | 4/1994 | Brown | 364/413.09 |
| 5,628,309 | 5/1997 | Brown | 128/632 |
| 5,792,117 | 8/1998 | Brown . | |
| 5,997,502 | 12/1999 | Reilly et al. . | |

*Primary Examiner*—Mark Bockelman
*Attorney, Agent, or Firm*—Black Lowe & Graham PLLC

[57] ABSTRACT

Measurements of insulin quantities in a syringe are performed optically in an integrated insulin dose recorder/blood glucose meter. The syringe is placed in a holder before and after the administration of the dose. Liquid quantities in the syringe are determined by comparing optical response patterns of the syringe with calibration data stored in the device. Dose histories are downloaded to a patient computer for transfer to a clinician's computer. Standard or customized syringes (e.g. with marked plungers) may be used. Other wave energy carriers such as sound waves may also be used.

11 Claims, 6 Drawing Sheets

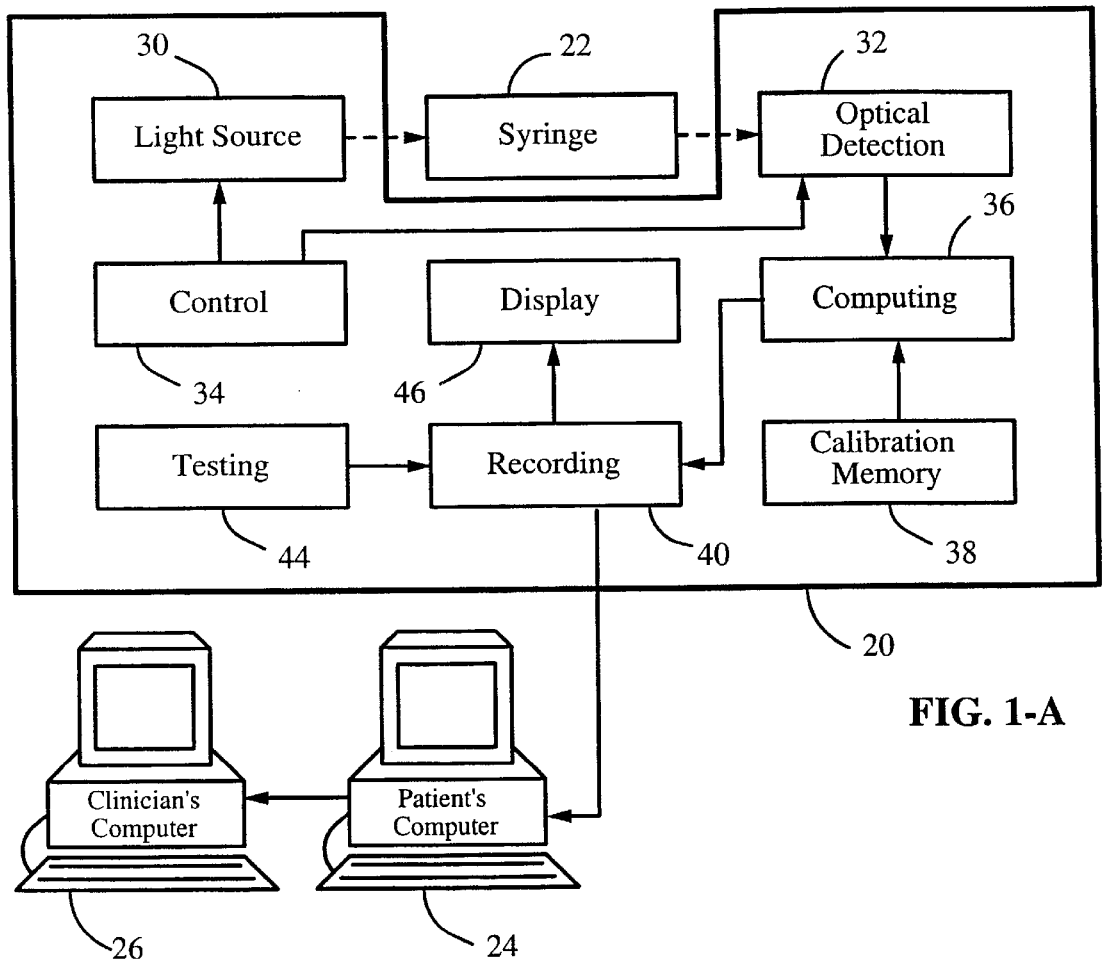
FIG. 1-A
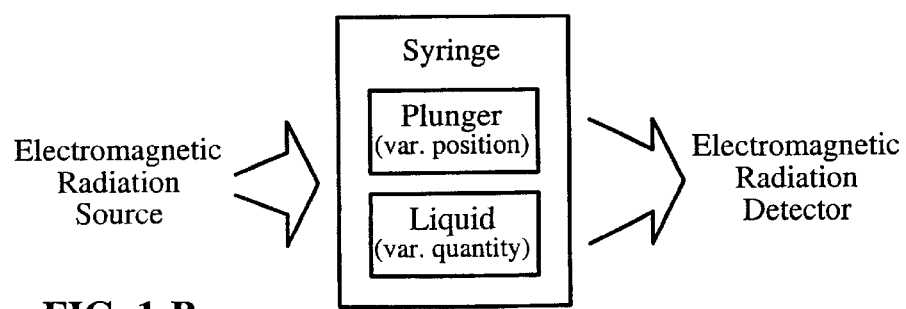
FIG. 1-B

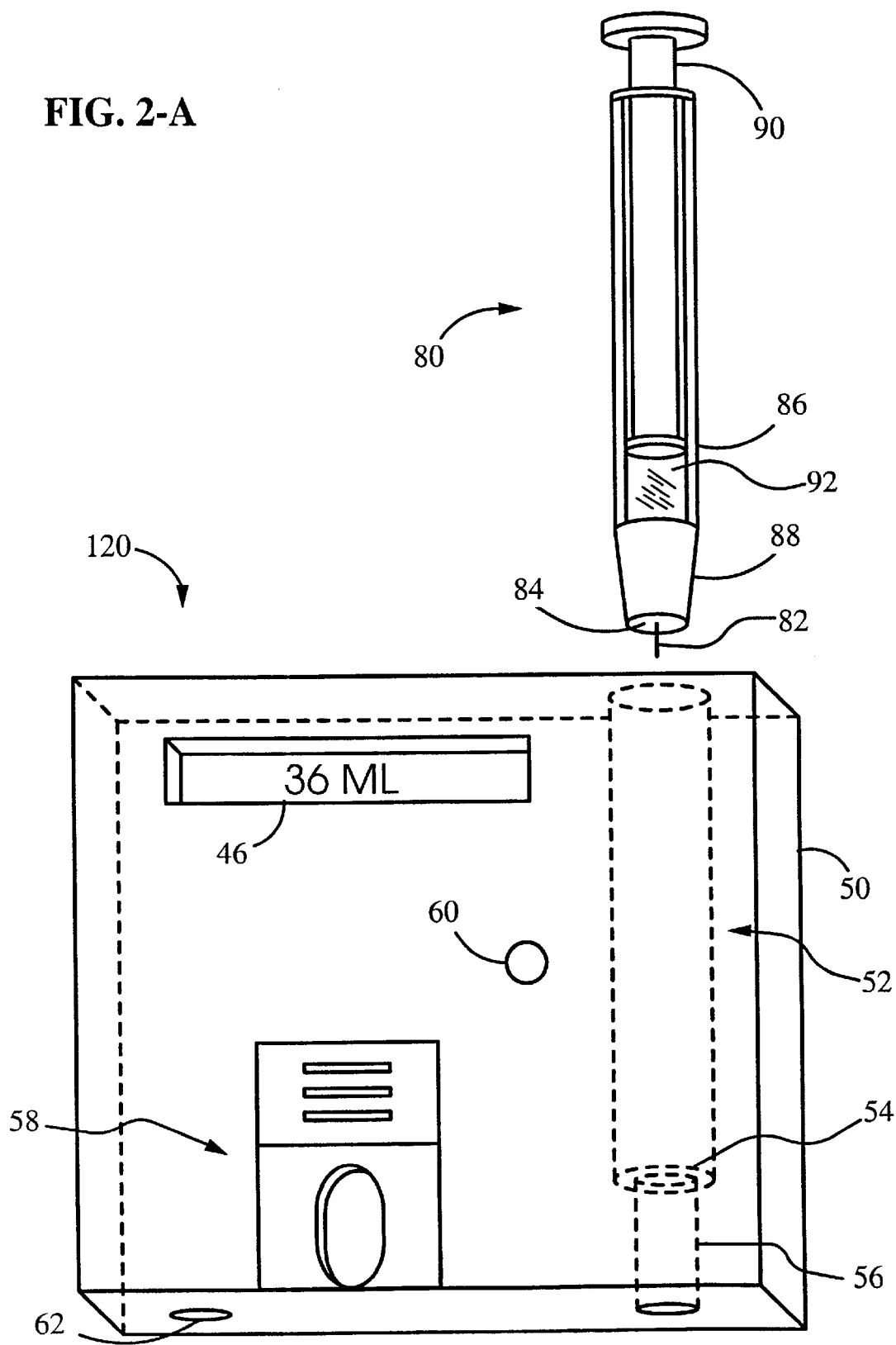
FIG. 2-A

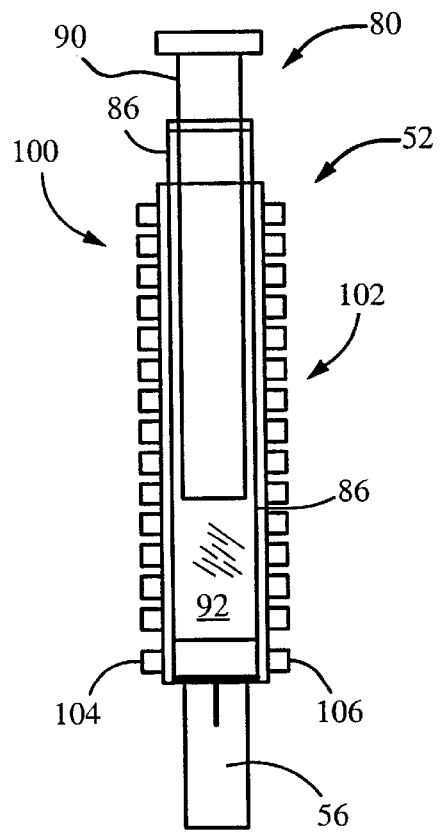
FIG. 2-B
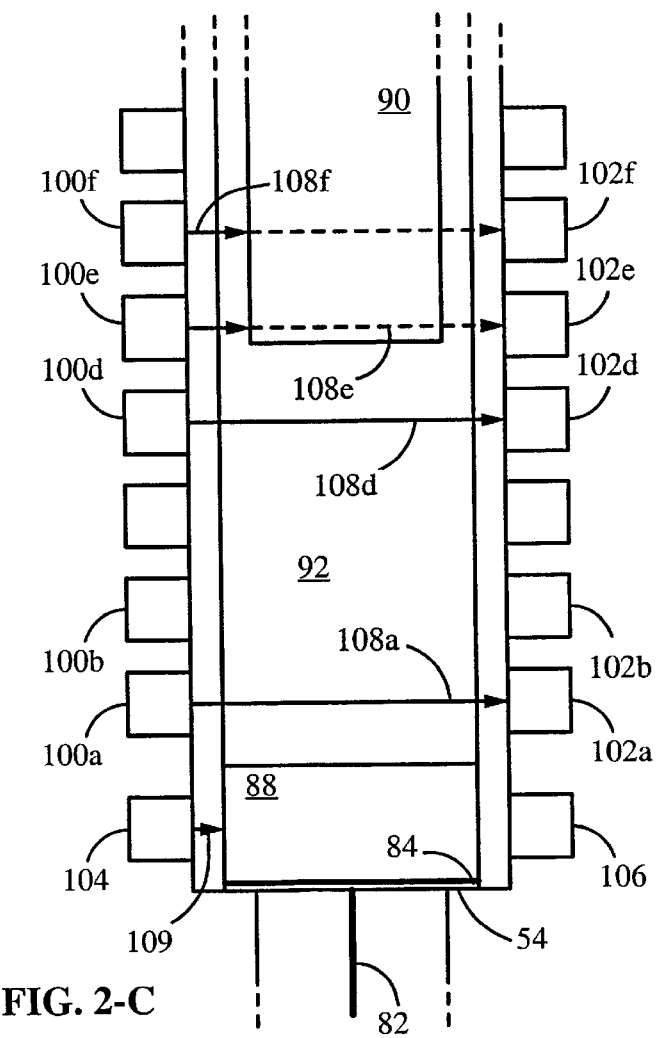
FIG. 2-C

FIG. 2-D
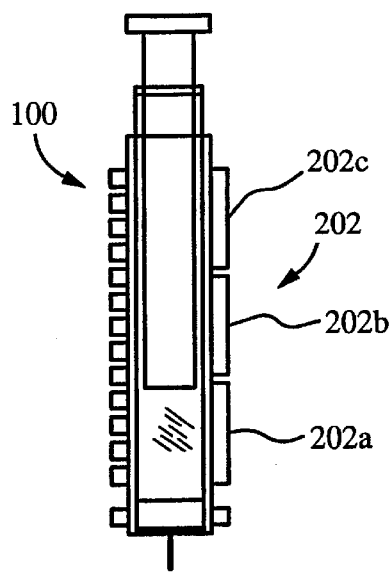
FIG. 2-E
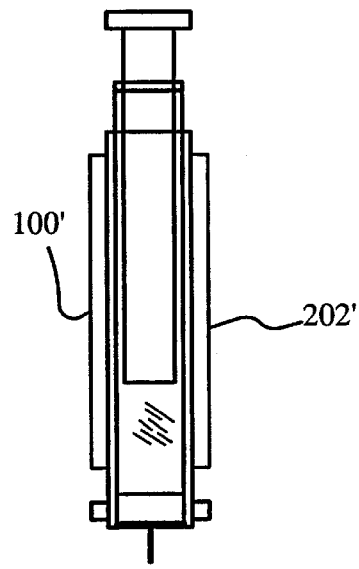
FIG. 3-B
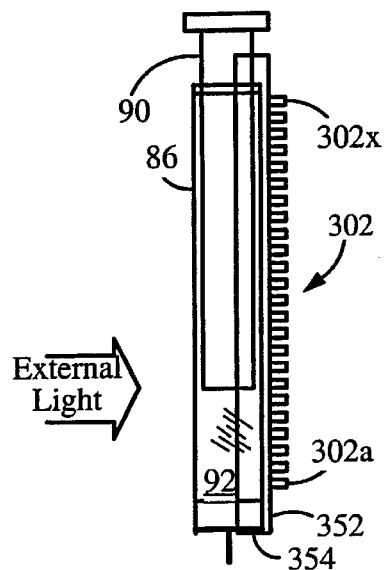

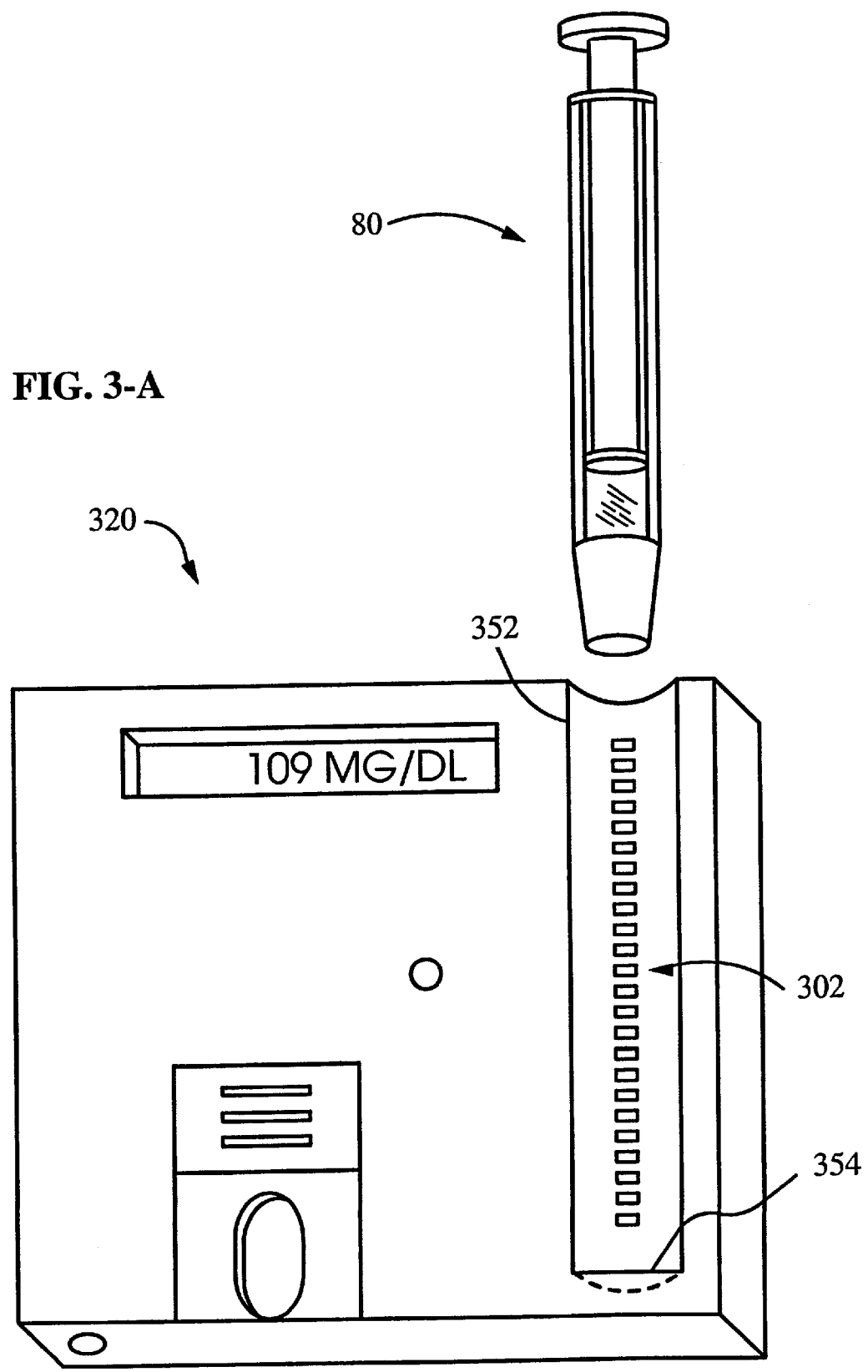
FIG. 3-A

OPTICAL DOSE MEASUREMENTS IN SYRINGES

RELATED APPLICATION DATA

This application is a divisional application of U.S. appl. Ser. No. 08/898,711 filed on Jul. 22, 1997 now abandoned. U.S. appl. Ser. No. 08/898,711 is a continuation-in-part, of co-pending U.S. patent application Ser. No. 08/681,223, filed Jul. 22, 1996 entitled "Apparatus for Optically Determining and Electronically Recording Injection Doses in Syringes," now U.S. Pat. No. 5,792,117 which is a continuation-in-part of U.S. patent Application Ser. No. 08/278,929, filed Jul 22, 1994, (now U.S. Pat. No. 5,569,212) and is related to U.S. patent application Ser. No. 08/591,308 (now U.S. Pat. No. 5,628,309). This application is related to U.S. patent application Ser. No. 08/681,314 now U.S. Pat. No. 5,720,733 and Ser. No. 08/681,290 now U.S. Pat. No. 5,782,814. All of the above applications are assigned to the assignee of the present invention, and are herein incorporated by reference.

FIELD OF THE INVENTION

This invention relates to injection syringes and patient monitoring devices, and in particular to an apparatus for optically determining and electronically recording doses of an agent delivered with an injection syringe.

BACKGROUND OF THE INVENTION

In recent years, the value of keeping electronic medical records in place of paper records has been widely recognized in the health care industry. The use of electronic medical records allows health care providers and patients to store, retrieve, and share medical information with considerably more ease and accuracy. The sharing of medical information is particularly important in treatment programs involving the injection of insulin, human growth hormone, or other medications.

Typically, these injections are performed using disposable syringes. Unfortunately, no adequate apparatus exists that measures and electronically records dose information from a disposable syringe. As a result, the patient or health care worker performing the injection is burdened with the task of injecting the dose and then manually recording the dose amount in a log book.

Because of the frequency of such injections, often several times a day for diabetics, it becomes difficult to keep accurate records. Indeed, studies have shown that a patient's own records and recollections are often incomplete and inaccurate. Additionally, a patient may intentionally cheat while making self-recorded entries in an attempt to create a log book that will please his or her doctor. In the long-term this makes patient monitoring extremely difficult and jeopardizes the treatment program, possibly even endangering the patient's life.

Attempts have been made at developing electronic management systems for assisting patients in self-administered drug programs. For example, U.S. Pat. No. 5,019,974 issued to Beckers describes a hand-held, microprocessor-based recorder that interfaces with a master computer. The patient enters therapy information into the recorder via a keyboard. The recorder includes a display for displaying treatment therapy guidelines to the patient. The recorder also has a blood glucose meter for recording the patient's blood glucose levels.

The recorder described by Beckers does not automatically measure and record dose information from a disposable syringe. After injecting a dose, the patient must manually enter the dose information into the recorder using switches or keys. Although this is an improvement over keeping written records on paper, the effectiveness of the drug program is still limited by the patient's recollections and recordings, which are unreliable.

Attempts have also been made at developing devices that deliver a predetermined dose of medication and record the dose amount. For example, U.S. Pat. No. 5,176,502 issued to Sanderson et al. on Jan. 5, 1993 describes a syringe pump for expelling a preset dose of medication from a syringe. The syringe pump includes a syringe retainer for holding the syringe and a driver for engaging the plunger of the syringe. An electric motor pushes the driver and plunger into the syringe barrel to expel the medication.

The syringe pump further includes a monitoring circuit for monitoring the motion of the driver during the delivery of the medication. The monitoring circuit includes a linear potentiometer having an electrically conductive strip of resistive material. The resistive material is positioned such that it engages an electrical contact of the driver. The position of the electrical contact on the resistive strip varies the voltage of the monitoring circuit, thus indicating the position of the plunger inside the barrel. A microprocessor receives voltage signals from the monitoring circuit and compares the voltage signals to preprogrammed signals to determine if the plunger displacement corresponds to correct displacement for delivering the preset dose. A control mechanism connected to the microprocessor regulates the driver's movement to ensure the preset dose of medication is delivered.

Although the syringe pump described by Sanderson does allow electronic recording of dose information, it is only designed to deliver medication directly into an intravenous line. It is not designed to inject a patient directly nor can it measure and record a dose from a syringe unless the syringe pump pushes the plunger. Consequently, the syringe pump is of little use to a health care worker who must inject a patient directly, or to an outpatient who must follow a self-injection treatment program.

Another device for injecting a preset dose of medication and for recording the injected dose is disclosed in U.S. Pat. No. 4,950,246 issued to Muller on Aug. 21, 1990. Muller describes a battery-operated injection pen having a pump rod driven by an electric motor. The electric motor is controlled by an electronic control unit that includes a microprocessor with a memory for storing dose information. The injection pen further includes a sensor connected to the control unit for electrically determining the position of the pump rod, and thus the amount of medication injected.

Although the injection pen described by Muller measures and electronically records dose information, it has several disadvantages that have precluded its widespread use. The injection pen is an expensive device requiring complicated electronic equipment to deliver and record doses. Moreover, because the injection pen integrates a syringe and electronic recorder into one device, it is not disposable. The patient must use it repeatedly for each injection, even after the injection pen has been contaminated with blood. Consequently, the injection pen does not provide an inexpensive, convenient, or hygienic solution to patients wishing to measure and electronically record injected dose information.

U.S. Pat. No. 4,853,521 issued to Ronald Claeys on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

Operating the device described by Ronald Claeys requires many complicated steps of weighing syringes, scanning in bar codes, etc. The complexity of the required procedures as well as the high cost of the apparatus have precluded its widespread use. Additionally, the device cannot be easily carried by the user for recording doses while away from the health care facility or home. Thus, no inexpensive apparatus exists for determining and electronically recording dose information from a disposable syringe. Further, no such apparatus exists that is both simple in operation and easily carried by a user.

OBJECTS AND ADVANTAGES OF THE INVENTION

It is a primary object of the present invention to provide an apparatus for optically determining and electronically recording an injection dose delivered from a disposable syringe. It is another object of the invention to provide an apparatus that may be easily operated and carried by a user. A further object of the invention is to suit the apparatus to diabetic patients, and to diabetes home care in particular.

It is yet another object to provide an apparatus facilitating automated paperless data processing, from the measurement performed by the patient to the recording at the clinic. These and other objects and advantages will become more apparent after consideration of the ensuing description and drawings.

SUMMARY OF THE INVENTION

The present invention provides an apparatus for non-invasively measuring and electronically recording a dose of an agent delivered with a syringe. The apparatus comprises a holding means for receiving and holding the syringe, a light source attached to the holding means and in optical communication with the syringe, an optical detector in optical communication with the syringe, and a recording means in electrical communication with the optical detector. An alignment means such as an alignment ledge aligns the syringe barrel to the optical detector and/or the light source, when the syringe is in a measurement position.

The light source generates light incident on the syringe. An optical response of the syringe to the incident light is indicative of the liquid quantity within the syringe, and implicitly of the dose administered (or to be administered) with the syringe. The optical detector detects the optical response. The recording means records a dose datum indicative of the optical response, and implicitly indicative of the dose. The dose can be computed from the dose datum given available (measured and/or calculated) data such as other dose, calibration, or syringe parameter data.

The incident light preferably comprises wavelengths that are suitable for measuring typical plunger displacements (resolution on the order of 0.1 mm to 1 mm) and/or liquid quantities within the syringe (resolution on the order of 0.1 $cm^3$), and that interact minimally with elements (e.g. barrel) which do not vary with the quantity of liquid within the syringe. Such wavelengths are preferably, but generally need not be, in visible or near-visible (infrared/ultraviolet) ranges. Preferably, the detector is suitable for detecting light within a range of wavelengths emitted by the light source. Generally, the wavelength range emitted by the light source need not be identical to the wavelength range detected by the detector. In fact, the wavelength ranges need not even overlap, if the light detected by the detector results from absorption and re-emission by the syringe.

The light source and detector preferably comprise semiconductor emitting/detecting devices, but generally may include any device capable of emitting/detecting light of desired wavelengths. Such devices may include antennas or heat sensors. The recording means comprises an electronic memory, preferably a digital memory unit.

The detector preferably comprises a plurality of longitudinally-spaced individual optical detecting elements coupled to the holding means and in optical communication with the syringe. The detecting elements detect an optical response pattern of the syringe, i.e. a spatial distribution of the syringe response. Dose data indicative of the optical response pattern is then recorded. The light source preferably comprises plural longitudinally-spaced light emitters. Each light emitter generates a light beam incident on the syringe. The optical response pattern is indicative of the interaction of the light beams with the syringe. Preferably, each of the light emitters is substantially aligned longitudinally with one of the detecting elements. If a control means in electrical communication with each of the light emitters is used to individually control each of the light emitters, a separate response pattern may be recorded for each emitter.

In an embodiment which does not require an internal light source, the holding means encloses the syringe only on one side. The holding means does not completely enclose the syringe on the side opposite the detector, so as to allow external light to be incident on the syringe. The response pattern detected by the detector is then dependent on the interaction between the external light and the syringe.

In one embodiment, the syringe comprises a response-enhancing element comprising an optical marking. The optical response of the syringe depends on the interaction of incident light with the marking, and on the position of the marking. The position of the marking is indicative of the dose. The response-enhancing element may comprise a longitudinal element mechanically coupled to (e.g. on the surface of, or within) the syringe plunger. The longitudinal element is longitudinally marked by the marking. The marking may be a shape marking, or a color marking varying longitudinally in brightness and/or hue.

If the detector detects light transmitted or emitted by the syringe, the detector is situated opposite the light source relative to the syringe. If the detector detects light reflected by the syringe, the detector is situated adjacent the light source relative to the syringe (on the same side of the syringe).

A port connected to the recording means allows downloading dose data histories from the recording means to a host computer (storage and communications device). A display connected to the detector and/or recording means displays dose data including current doses and dose histories to the patient.

Generally, the recording means may record any signal indicative of the optical response detected by the detector. For example, the recording means may record directly the optical response signal generated by the detector. Doses are then computed on a distinct computer after downloading of the recording means contents to the computer. Preferably, however, a computing means computes the dose data recorded by the recording means from the optical response by the detector.

Preferably, a housing encloses the light source, detector, recording means, and testing means. The holding means is mechanically coupled with the housing, and is preferably enclosed by the housing. The housing is sufficiently compact to be hand-held and carried by the user, preferably having a size on the order of centimeters and a weight on the order of hundreds of grams. The device is preferably battery-powered.

DESCRIPTION OF THE FIGURES

FIG. 1-A is a high-level schematic diagram illustrating the structure of a preferred apparatus of the present invention.

FIG. 1-B illustrates broadly the principal detection step performed by an apparatus of the present invention.

FIG. 2-A is a perspective view of a preferred apparatus of the present invention.

FIG. 2-B is a longitudinal sectional view of a syringe situated in a measurement position in a holder of the apparatus of FIG. 2-A, illustrating a preferred light source and detector arrangement.

FIG. 2-C shows a detail of FIG. 2-B, including the plunger-liquid interface within the syringe.

FIG. 2-D shows an alternative light source and detector arrangement in a view similar to that of FIG. 2-C, according to the present invention.

FIG. 2-E shows another alternative light source and detector arrangement in a view similar to that of FIG. 2-C, according to the present invention.

FIG. 3-A shows an apparatus which does not require an internal light source, according to an alternative embodiment of the present invention.

FIG. 3-B shows a longitudinal sectional view of a syringe situated in a measurement position in a holder of the apparatus of FIG. 3-A.

DETAILED DESCRIPTION

Figure 4:
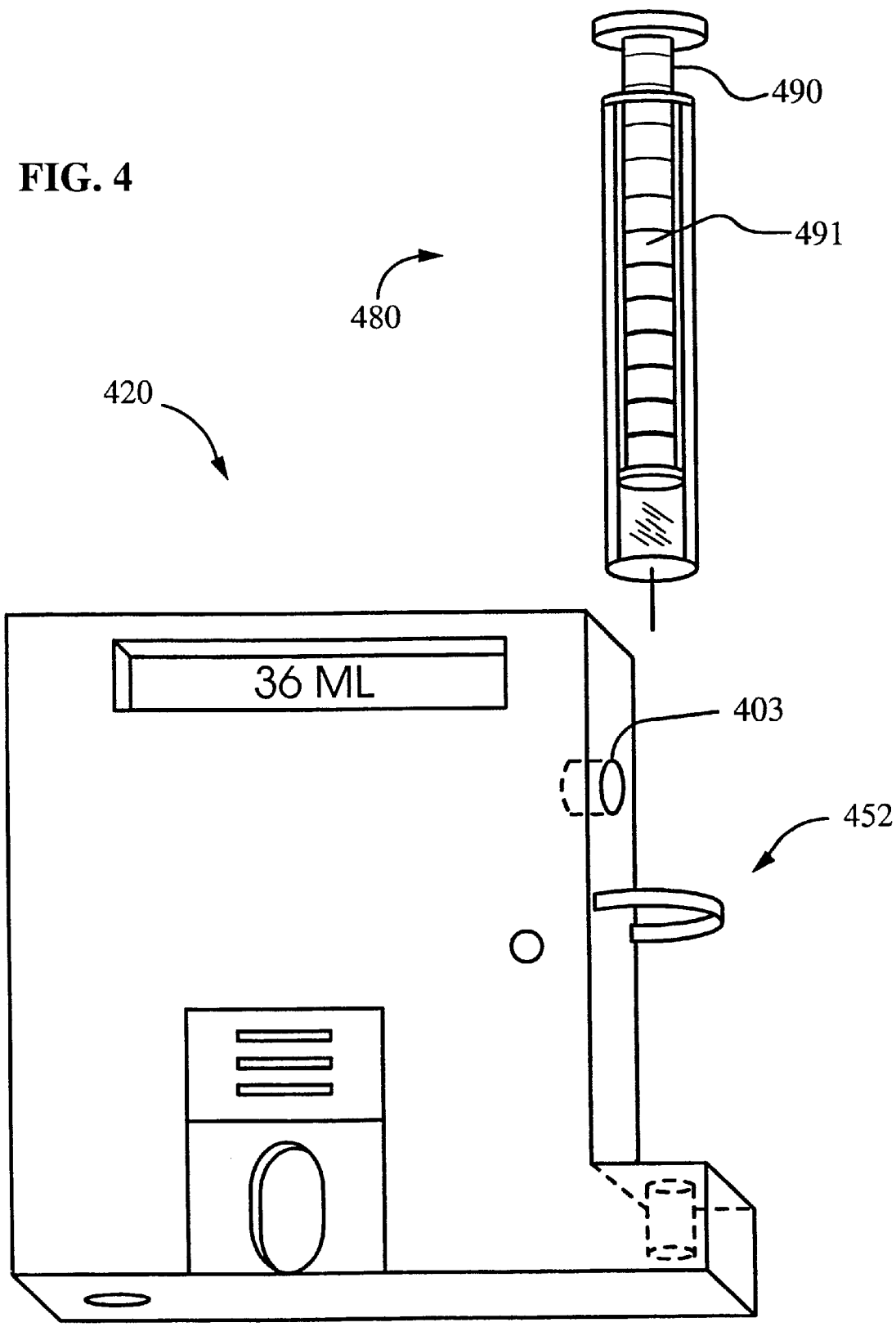
FIG. 4 shows a perspective view of an embodiment comprising a plunger having a longitudinally-varying marking, according to the present invention.

FIG. 1-A is a high-level schematic diagram illustrating a preferred apparatus 20 of the present invention. Optical connections are illustrated by dashed lines, electrical connections by solid lines. Apparatus 20 records data indicative of doses delivered to a patient using a syringe 22. Apparatus 20 is capable of downloading the recorded data to a patient computer 24, which in turn is capable of communicating with a clinician's computer 26 over a telephone line or the Internet.

Apparatus 20 comprises a light source 30 and an optical detector 32 in optical communication with syringe 22. Light source 30 generates light incident on syringe 22. Optical detector 32 detects an optical response of syringe 22 to the light generated by light source 30. The optical response of syringe 22 is indicative of the quantity of liquid in syringe 22, and consequently of the dose administered to the patient using syringe 22. A control means 34 in electrical communication with light source 30 and optical detector 32 temporally controls the operation of light source 30 and optical detector 32. Control means 34 turns on light source 30 and optical detector 32 when syringe 22 is appropriately positioned for dose measurements, before and after the administration of the dose to the patient.

A computing means 36 is in electrical communication with optical detector 32 and with a calibration memory 38. Computing means 38 is further in electrical communication with a recording means 40. Computing means 36 generates dose data to be stored in recording means 40. The dose data preferably comprises a dose (e.g. insulin dose) administered to the patient, but may be in general any data which can be used to reconstruct (for example within apparatus 20, at patient computer 24, or at clinician computer 26) the dose administered to the patient. In particular, computing means 36 calculates quantities of liquid within syringe 22 before and after injection of a dose. Computing means 36 then calculates the difference between the two measured liquid quantities, and sends the result (the dose) to recording means 40 for storage. Computing means 36 determines liquid quantities by comparing optical response data received from optical detector 32 with predetermined calibration data stored in calibration memory 38. The calibration data is indicative of the correspondence between optical responses and liquid quantities for the entire range of potential liquid quantities in syringe 22. That is, calibration memory 38 stores the liquid quantity corresponding to a given optical response of detector 32, for all liquid quantities potentially present in syringe 22.

A testing means 44 is electrically connected to recording means 40. Testing means 44 tests a physical condition of the patient, and generates condition data representative of the physical condition. Preferably, the physical condition is diabetes, the testing means comprises a conventional blood glucose meter, and the condition data comprises a blood glucose level of the patient. Recording means 40 records the condition data generated by testing means 44. A display 46 is electrically connected to recording means 40, and displays dose data and condition data to the patient. Note that a display such as display 46 may be in general directly connected to computing means 36 and testing means 44, rather than indirectly through recording means 40.

FIG. 1-B illustrates generally the principal detection step performed by an apparatus of the present invention. Light (electromagnetic radiation) is incident on syringe 22 and interacts with syringe 22. Light resulting from the interaction is then incident on a detector. The light incident on the detector may generally be light transmitted, reflected, and/or emitted by syringe 22. In general, two elements of syringe 22 may vary with the quantity of liquid within syringe 22 in a typical dose administration sequence: the position of the syringe plunger (relative to the syringe barrel), and the quantity/position of the liquid within syringe 22. Light incident on syringe 22 may interact with the plunger and/or liquid. The measured light interaction with the plunger is preferably substantially different from the interaction with the liquid, such that the interaction with syringe 22 as a whole depends on at least one of the position of the plunger and the quantity of liquid.

FIG. 2-A shows a perspective view of an apparatus 120, according to a preferred embodiment of the present invention. Apparatus 120 comprises a housing 50 enclosing the various electronic and optical components of apparatus 120. Display 46 is recessed within housing 50. A patient interface 58 of testing means 44 is also coupled to housing 50. The patient places his or her finger on patient interface 58, allowing testing means 44 to perform a blood glucose measurement for the patient. Blood glucose meters are well known in the art and will not be discussed here in detail. A dose measurement control 60 of control means 34 is coupled to housing 50, and allows the patient to specify when dose measurements are to be performed by apparatus 120 (see below).

Housing 50 also encloses a holding means 52 for receiving and holding a syringe 80. Syringe 80 is preferably a conventional plastic syringe. Syringe 80 comprises a barrel 86 and a plunger 90, defining a space for a liquid 92. Plunger 90 is capable of longitudinal motion relative to barrel 86, for adjusting the volume available to liquid 92. Barrel 86 has side walls transparent at a wavelength of light emitted by a light source, as well as a control portion 88 opaque at a wavelength of light emitted by a control emitter (see below).

Holding means 52 comprises an alignment ledge 54 for aligning barrel 86 to holding means 52 in a predetermined measurement position. A contact surface 84 of syringe 80 is in contact with alignment ledge 54 when syringe 80 is in the measurement position (see below). A space 56 accommodates a needle 82 of syringe 80, when syringe 80 is in the measurement position.

FIG. 2-B shows a longitudinal sectional view through syringe 80 and holding means 52, with syringe 80 in a measurement position. A light source 100 and an optical detector 102 are mechanically coupled to holding means 52 and in optical communication with syringe 80. Optical detector 102 is opposite light source 100 relative to syringe 80, such that optical detector 102 detects light transmitted through syringe 80. Light source 100 generates light incident on both plunger 90 and liquid 92. A control light source 104 and a control optical detector 106 of control means 34 are mechanically coupled to holding means 52, and are in optical communication with control portion 88 when syringe 80 is in the measurement position.

FIG. 2-C shows a detail of FIG. 2-B. Following a patient command entered by the patient pressing dose measurement control 60, control light source 104 emits a light beam 109 which is blocked by control portion 88 when syringe 80 is in the measurement position. If light beam 109 is blocked, control means 34 operates light source 100 and detector 102 to take a first liquid quantity measurement, before the injection of liquid 92 by the patient. Light beam 109 is then incident on control detector 106 while syringe 80 is out of holding means 52. When the patient inserts syringe 80 into holding means 52 after the injection of a dose of liquid 92, light beam 109 is again blocked, and control means 34 operates light source 100 and detector 102 to take a second liquid quantity measurement. The difference between the two liquid quantities is taken to be the dose injected by the patient, and is stored by recording means 40.

Light source 100 comprises a plurality of light emitters 100a–f, while detector 102 comprises a plurality of detecting elements 102a–f. Light emitters 100a–f and detecting elements 102a–f are longitudinally spaced apart at regular intervals. Each light emitter 100a–f is longitudinally aligned to a corresponding detecting element 102a–f. Light emitters 100a–f are preferably narrow-angle light emitting diodes (LEDs), while detecting elements 102a–f are preferably photodiodes capable of detecting light of a wavelength emitted by light emitters 100a–f.

For detecting the quantity of liquid 92 within syringe 80, light emitters 100a–f emit light beams 108a–f incident on plunger 90 and liquid 92. Detector elements 102a–f detect the resulting optical response pattern of syringe 80. Emitter 100d, situated under the current position of plunger 90, emits a light beam 108d which passes through liquid 92 and is incident on detector 102d. Emitter 100e, situated above the current position of plunger 90, emits a light beam 108e which is incident on plunger 90. Plunger 90 has a substantially different optical transmission property from liquid 92 at the wavelength(s) measured by detecting element 102e. Preferably, plunger 90 is opaque at those wavelengths. Plunger 90 then substantially blocks beam 108e, such that beam 108e is not incident on detecting element 102e.

An electrical signal indicative of the optical pattern detected by detector 102 is sent to computing means 36.

FIG. 2-D illustrates an alternative geometry for a detector of the present invention. A detector 202 comprises detecting elements 202a–c, each of which receives light emitted by plural emitters of light source 100. FIG. 2-E illustrates yet another geometry for a light source and detector of the present invention. A light source 100' and a detector 202' each comprise a single emitting or detecting element, extending longitudinally over the range of potential plunger bottom positions. The total amount of light detected by detector 202' is indicative of the plunger position-relatively little light is incident on detector 202' if the plunger occludes the light path between light source 100' and detector 202'. The single-element detecting scheme illustrated in FIG. 2-E can be less sensitive than a multiple-element detecting scheme using similar components, but is advantageous because of its simple design.

FIG. 3-A shows a perspective view of another embodiment of the present invention. An apparatus 320 comprises a holding means 352 which encloses syringe 80 only on one side when syringe 80 is in a measurement position. FIG. 3-B shows a side longitudinal view of the holding means 352 and syringe 80 in the measurement position. A control ledge 354 aligns the barrel of syringe 80 with a detector 302 in the measurement position. Detector 302 comprises plural longitudinally-spaced detecting elements 302a–x. To take measurements, the patient orients the measurement face of holding means 352 toward an external source of spatially uniform light, preferably a parallel light beam. For example, the patient places apparatus 352 close to a bright window or lamp. For the embodiment in FIG. 3-A, the computing means calculates quantities of liquid within syringe 80 according to the distribution of signals received from the detecting elements of detector 302, rather than the absolute values of the signals.

FIG. 4 shows a perspective view of another alternative embodiment of the present invention. An apparatus 420 comprises a holding means 452 for holding the barrel of a syringe 480 in an predetermined position relative to a measurement window 403. Syringe 480 comprises a plunger 490 having a longitudinally-varying marking 491. Marking 491 is desirably a color marking, but generally may be a shape marking. A light source and detector are situated behind measurement window 403, for reading the part of marking 491 in front of window 403. Light emitted by the light source is reflected by marking 491 back into the detector. The reflected light (its intensity and/or spatial distribution) is indicative of the position of marking 491 relative to window 403, which is in turn indicative of the quantity of liquid within syringe 480.

It will be clear to one skilled in the art that the above embodiments may be altered in many ways without departing from the scope of the invention. Generally, the dose data may include, for example, quantities of liquid in the syringe before and after the administration of the dose, or optical response values generated by the optical detector(s) before and after the administration of the dose; the patient's and/or the clinician's computers then determine the dose administered to the patient from the dose data stored in the recording means. In such an embodiment, calibration data may be stored on the patient's or clinician's computer, and the apparatus may lack a computing means. The patient computer need not be a conventional personal computer, but can be in general any device allowing communication between the patient's measurement apparatus and the clinician's data storage device or server. An apparatus of the present invention may connect directly to a clinician's server, rather than indirectly through a patient computer.

Detecting spatial distributions is useful for increasing sensitivity. The detector need not detect a spatial distribution of light, however. The detector may detect a spatial sum of light intensity over a whole area, as long as that spatial sum is indicative of the dose administered with the syringe. For example, the detector may detect the total amount of light passing through the syringe, or the total amount of light emitted by the syringe following absorption of incident light (e.g. the total amount of heat emitted following exposure to microwave radiation). Moreover, light emitting and detecting elements need not be longitudinally spaced or aligned, and light beams need not be transverse to the longitudinal axis of the syringe. Various light source and detector geometries and placements may be suitable in a device of the present invention.

The method does not require the presence of a plunger to transmit, reflect or absorb light. A method of the present invention may be used to optically measure liquid levels in plungerless syringes operated using air pressure, for example.

The methods and devices described above may be extended to non-optical wave energy forms such as sound (non-electromagnetic) waves. The considerations discussed above for choosing frequency and detector parameters for optical detectors largely apply to an apparatus using sound wave detection. For example, suitable sound frequencies may include frequencies for which sound absorption by water is significantly (e.g. at least by a factor of two) different from absorption by the syringe plunger. Sound frequencies above the hearing range may be desirable so as to avoid disturbing the user.

Accordingly, the scope of the invention should be determined by the following claims and their legal equivalents.

What is claimed is:

1. An apparatus for optically measuring and electronically recording a dose, said apparatus comprising:
    a) a holding means for receiving and holding a syringe in a measurement position;
    b) a light source in optical communication with the syringe, said light source for generating light incident on the syringe when the syringe is in the measurement position;
    c) an optical detector positioned to detect a total amount of said light that is transmitted through said syringe; and
    d) a recording means in electrical communication with said optical detector, said recording means for recording a dose datum indicative of said total amount of said light that is transmitted, wherein said dose datum is indicative of said dose.

2. The apparatus of claim 1, further comprising an alignment means for aligning the syringe with said optical detector when the syringe is in the measurement position.

3. The apparatus of claim 1, further comprising a housing, said housing enclosing said light source, said optical detector, and said recording means; wherein said housing is sufficiently compact to be hand-held and carried by a patient.

4. An apparatus for optically measuring and electronically recording a dose delivered with a syringe, said aparatus comprising:
    a) an optical detector in optical communication with the syringe, said optical detector for measuring a total amount of light transmitted through said syringe, wherein said total amount of light transmitted is indicative of a quantity of liquid in the syringe, said quantity of liquid being indicative of the dose; and
    b) a recording means in electrical communication with said optical detector, for recording a dose datum indicative of said total amount of light transmitted, wherein said dose datum is indicative of said dose.

5. The apparatus of claim 4, further comprising a light source for generating light incident on the syringe.

6. The apparatus of claim 4, further comprising a computing means and a calibration memory means, said computing means in electrical communication with said optical detector, with said recording means, and with said calibration memory means.

7. The apparatus of claim 4, further comprising a housing, wherein said optical detector occupies a fixed spatial relationship to said holding means, and said holding means is mechanically coupled to said housing.

8. The apparatus of claim 7, wherein said holding means is external to said housing.

9. The apparatus of claim 7, wherein said holding means is internal to said housing.

10. A diabetes monitoring and insulin dose recording apparatus, comprising:
    a) a holding means for receiving and holding a syringe containing insulin;
    b) a light source coupled to said holding means and in optical communication with the syringe, for generating light incident on the syringe;
    c) an optical detector in optical communication with the syringe, for detecting a total amount of said light that is transmitted through said syringe;
    d) a computing means in communication with said optical detector, for computing a dose datum indicative of the insulin dose from said total amount of said light that is transmitted;
    e) a blood glucose meter for determining a blood glucose datum indicative of a blood glucose level; and
    f) a recording means in electrical communication with said computing means and said blood glucose meter, for recording said dose datum and said blood glucose datum.

11. The apparatus of claim 10, further comprising a port connected to said recording means, for transmitting said dose datum and said blood glucose datum from said recording means to a host computer.

* * * * *

UNITED STATES PATENT AND TRADEMARK OFFICE
CERTIFICATE OF CORRECTION

PATENT NO. : 6,113,578
DATED : September 5, 2000
INVENTOR(S) : Stephen J. Brown

Page 1 of 1

It is certified that error appears in the above-identified patent and that said Letters Patent is hereby corrected as shown below:

<u>Title page,</u>
Item [60], The paragraph entitled, "Related U.S. Application Data" is amended to read as follows:

Division of application No. 08/898,711, Jul. 22, 1997, abandoned, which is a continuation-in-part of application No. 08/681,223, Jul. 22, 1996, Pat. No. 5,792,117, which is a continuation-in-part of application No. 08/278,929, Jul. 22, 1994, Pat. No. 5,569,212.

Signed and Sealed this

Eleventh Day of June, 2002

*Attest:*

JAMES E. ROGAN
*Attesting Officer*       *Director of the United States Patent and Trademark Office*